US010983595B2

(12) United States Patent
Zhang et al.

(10) Patent No.: US 10,983,595 B2
(45) Date of Patent: Apr. 20, 2021

(54) COMPUTER SYSTEM FOR ACQUIRING A CONTROL COMMAND

(71) Applicant: Agency for Science, Technology And Research, Singapore (SG)

(72) Inventors: Zhuo Zhang, Singapore (SG); Cuntai Guan, Singapore (SG); Chuanchu Wang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 16/498,872

(22) PCT Filed: Mar. 29, 2018

(86) PCT No.: PCT/SG2018/050163
§ 371 (c)(1),
(2) Date: Sep. 27, 2019

(87) PCT Pub. No.: WO2018/182534
PCT Pub. Date: Oct. 4, 2018

(65) Prior Publication Data
US 2020/0057499 A1    Feb. 20, 2020

(30) Foreign Application Priority Data

Mar. 31, 2017    (SG) ............... 10201702705R (51) Int. Cl.
*H04B 3/46* (2015.01)
*G06F 3/01* (2006.01)
(Continued)

(52) U.S. Cl.
CPC .......... *G06F 3/015* (2013.01); *A61B 5/04842* (2013.01); *G05B 15/02* (2013.01)

(58) Field of Classification Search
CPC ... G06F 3/015; A61B 5/04842; A61B 5/7246; A61B 5/0476; G05B 15/02
See application file for complete search history.

(56) References Cited

U.S. PATENT DOCUMENTS

2013/0245485 A1*   9/2013   Mashour ............ A61B 5/74
                                                600/544
2013/0338738 A1    12/2013  Garcia Molina et al.
(Continued)

FOREIGN PATENT DOCUMENTS

CN    102722244 A    10/2012
CN    103440039 A    12/2013

OTHER PUBLICATIONS

Won D. et al., A BCI speller based on SSVEP using high frequency stimuli design. 2014 IEEE International Conference on Systems, Man, and Cybernetics, Oct. 8, 2014, pp. 1068-1071 [Retrieved on Apr. 23, 2018] <DOI: 10.1109/SMC.2014.6974055> whole document.

(Continued)

*Primary Examiner* — Dhaval V Patel
(74) *Attorney, Agent, or Firm* — Womble Bond Dickinson (US) LLP; John J. Penny, Jr.

(57) ABSTRACT

A computer system for acquiring a control command. The system includes one or more processors in communication with non-transitory data storage media having instructions stored thereon that, when executed by the one or more processors, configure the one or more processors to perform particular steps. The steps include: receiving, at an electro-encephalogram (EEG) receiver, baseline EEG data; and acquiring, using a normalisation module, one or more normalisation factors from the baseline EEG data. The steps further include: receiving, at the EEG receiver, stimulated EEG data sensed by one or more EEG sensors; and correlating the stimulated EEG data across the one or more EEG
(Continued)

sensors, using a correlation module, to generate one or more correlation coefficients corresponding to one or more stimulation frequencies, each of the one or more stimulation frequencies corresponding to a respective candidate control command.

20 Claims, 8 Drawing Sheets

(51) Int. Cl.
    *A61B 5/0484*     (2006.01)
    *G05B 15/02*     (2006.01)

(56) References Cited

U.S. PATENT DOCUMENTS

2019/0232059 A1*   8/2019   Frohlich .............. A61N 1/0476
2019/0247654 A1*   8/2019   Alyagon .............. A61B 5/0006

OTHER PUBLICATIONS

International Search Report and Written Opinion mailed in corresponding International Application No. PCT/SG2018/050163, dated May 15, 2018.

* cited by examiner

Figure 1 a. Boxplot of correlation coefficient without spectrum b. Boxplot of correlation coefficient after spectrum flattening

```
% X -- multi-channel EEG
% Y -- reference signal
z = [X Y];
% calculate covariance
m = size(x,1);
C = (x' * x) / (m-1);
sx = size(X,1);
sy = size(Y,1);
Cxx = C(1:sx, 1:sx);
% calculate inversion matrix
invCxx = Inverse(Cxx);
Cxy = C(1:sx, sx+1:sx+sy);
Cyx = Cxy';
Cyy = C(sx+1:sx+sy, sx+1:sx+sy);
invCyy = inv(Cyy);
% calculate eigen value
[Wx,r] = Eigenvalues(invCxx*Cxy*invCyy*Cyx);
% canonical correlations
r = sqrt(real(r));
% return the first r
r1 = real(r(1));
```

COMPUTER SYSTEM FOR ACQUIRING A CONTROL COMMAND

The present application claims priority under 35 U.S.C. § 119 to Singaporean Application No. 10201702705R filed on Mar. 31, 2017, and under 35 U.S.C. § 365 to International Application No. PCT/SG2018/050163 filed on Mar. 29, 2018. The entire contents of these applications are incorporated herein by reference in their entirety.

FIELD OF THE INVENTION

The present invention relates to the acquisition of control commands from electroencephalogram (EEG) data.

BACKGROUND

In recent years, brain-computer interfaces (BCIs) are being developed as a means for identifying commands using EEG data rather than verbal or physical communication of those commands. Based on the brain activity patterns, EEG-based BCIs may be categorised into four different categories: event-related or event-based desynchronization/synchronization (ERD/ERS) BCIs, BCIs that use the P300 component of event related potentials (ERPs), BCIs that use slow cortical potentials (SCPs), and BCIs that use steady state visual evoke potentials (SSVEP).

SSVEP refers to brain signals which occur in response to visual stimulation. These signals may be triggered, for example, by a repeatedly flashing light emitted through a computer screen or LED. Viewing a flashing light at a particular frequency stimulates the visual pathway, causing the particular frequency to radiate throughout the brain.

This stimulation of the brain produces electrical signals at both the base frequency and multiples thereof—i.e. harmonics. For example: an image flashing at 5 hz should produce a response in the brain at frequencies of 5 Hz, 10 Hz, 15 Hz, . . . , etc. The identification of different underlying signals when viewing flashing lights with different frequencies, or when not viewing a flashing light, enables a self-paced BCI system. These signals can be identified using EEG techniques, EEG involving a recording of electrical signals measured on the scalp.

There are a number of uses for SSVEP technology, most notably is the cases of paralysis patients who can use these systems to interact with their environment. Such technology can be used, for example, in a text-based spelling system employing flashing lights to identify various words. Other interesting cases of SSVEP are uses in games such as spacecraft and maze.

In general, an SSVEP-based BCI aims to detect subjects' intention through recognizing the SSVEP frequency components in their brain waves, based on the fact that SSVEP is evoked over the occipital scalp region with the same frequency as the visual stimulus and its harmonics. Like other EEG modalities, SSVEP data can be contaminated by spontaneous EEG—brain waves generating during a subject's idle time, being time when the subject is not being stimulated by an SSVEP computer system—and other background noises in the brain.

Due to these limitations, existing SSVEP technologies have difficulty in accurately recognizing the frequency components of an EEG in a short time window.

Existing approaches to SSVEP recognition calculated power spectral density (PSD) at different frequencies within a specific time window. From this calculation, the target frequency was determined to be the frequency with the maximal PSD value. Since this approach operates on a signal EEG channel it is sensitive to noise and needs a relatively longer time window to facilitate accurate control command identification.

Other forms of SSVEP use canonical correlation analysis (CCA). With the CCA, correlation was improved or maximized between multi-channel EEG signals and the sine and cosine of reference signals at each of the stimulus frequencies. The stimulus frequency with the maximal correlation coefficient was assumed to be the target frequency. The use of CCA provided better SSVEP recognition performance than that of the PSDA since it delivered an optimization for the combination of multiple channels to improve the signal to noise ratio (SNR).

Many later methodologies were proposed to improve the basic CCA method for SSVEP-based BCI. Optimization was implemented on multi-channel and multi-trial EEG tensors to learn the reference signals in correlation analysis, for SSVEP recognition. Some of these techniques used L1-regularization imposed on a trial-way array optimization for effective trial selection to improve the reference signals. The addition of a penalty term and related calculations, to enable implementation of the L1-regularization methods, and other optimization techniques resulted in such methods requiring a tedious offline parameter tuning process to obtain the best set of parameters, either by grid search or by regularized optimization. Thus, these methods were unworkable in real-time.

It is desirable therefore to provide a method for identifying a subject's intent—e.g. an intended control command—that removes or ameliorates one or more of the abovementioned disadvantages of the prior art, or at least provides a useful alternative.

SUMMARY OF THE INVENTION

In accordance with the present disclosure, there is provided a computer system for acquiring a control command, the system including one or more processors in communication with non-transitory data storage media having instructions stored thereon that, when executed by the one or more processors configure the one or more processors to perform the steps of:

receiving, at an electroencephalogram (EEG) receiver, baseline EEG data;

acquiring, using a normalisation module, one or more normalisation factors from the baseline EEG data;

receiving, at the EEG receiver, stimulated EEG data sensed by one or more EEG sensors;

correlating the stimulated EEG data across the one or more EEG sensors, using a correlation module, to generate one or more correlation coefficients corresponding to one or more stimulation frequencies, each of the one or more stimulation frequencies corresponding to a respective candidate control command;

applying the one or more normalisation factors to the one or more correlation coefficients to produce one or more flattened correlation coefficients;

identifying, from the one or more stimulation frequencies and using the one or more processors, a control stimulation frequency based on the one or more flattened correlation coefficients; and acquiring, using a control command identification module, the control command by determining which said candidate control command corresponds to the control stimulation frequency.

In accordance with the present disclosure there is also provided a computer process for acquiring a control command, comprising:
    receiving baseline electroencephalogram (EEG) data;
    acquiring one or more normalisation factors from the baseline EEG data;
    receiving stimulated EEG data sensed by one or more EEG sensors;
    correlating the normalised EEG data across the one or more EEG sensors to generate one or more correlation coefficients corresponding to one or more stimulation frequencies, each of the one or more stimulation frequencies corresponding to a respective candidate control command;
    applying the one or more normalisation factors to the one or more correlation coefficients to produce one or more flattened correlation coefficients;
    identifying, from the one or more stimulation frequencies, a control stimulation frequency based on the one or more flattened correlation coefficients; and
acquiring the control command by determining which said candidate control command corresponds to the control stimulation frequency.

In accordance with the present disclosure there is further provided a computer process for generating a control command, comprising:
    receiving stimulated EEG data sensed by one or more EEG sensors;
    correlating the stimulated EEG data across the one or more EEG sensors using, for one or more stimulation frequencies, a plurality of phase-shifted signals of the stimulation frequency, to generate one or more correlation coefficients corresponding to the one or more stimulation frequencies, each of the one or more stimulation frequencies corresponding to a respective candidate control command;
    identifying, from the one or more stimulation frequencies, a control stimulation frequency based on the one or more correlation coefficients; and
    acquiring the control command by determining which said candidate control command corresponds to the stimulation frequency with the maximum correlation coefficient.

It will be appreciated that the broad forms of the invention and their respective features can be used in conjunction, interchangeably and/or independently, and reference to separate broad forms is not intended to be limiting.

Some embodiments of the present invention may address cross-subject heterogeneity of spectrum distribution characters i.e. variation in baseline EEG by providing spectrum flattening or spectrum normalisation.

Some embodiments of the present invention may address problems associated with subject-specific cortical response time lags by composing a library of phase shifting reference signals. These reference signals can be more readily used to identify a 'best-fit' where the subject-specific cortical response is out of phase with a base reference signal such as that used in the some existing methods.

Some embodiments facilitate optimization for any specific flickering source device i.e. at any flicker frequency by enabling the spectrum normalisation (i.e. spectrum flattening) to occur at desired control command frequencies.

Some embodiments of the present invention may provide a fast version or adaptation of a CCA algorithm for real-time signal processing.

BRIEF DESCRIPTION OF THE DRAWINGS

Preferred embodiments of the invention are hereafter described, by way of non-limiting example only, with reference to the accompanying drawings, in which.

DETAILED DESCRIPTION

It has been found that of the ERD/ERS, ERP, SCP and SSVEP categories or 'modalities' of BCI, an SSVEP-based BCI system requires the least training time. Moreover, SSVEP carries the fastest information transfer rate. Particularly in the computer processes described herein, SSVEP may also require fewer EEG channels to enable a reliable identification of control commands from EEG data.

Figure 1:
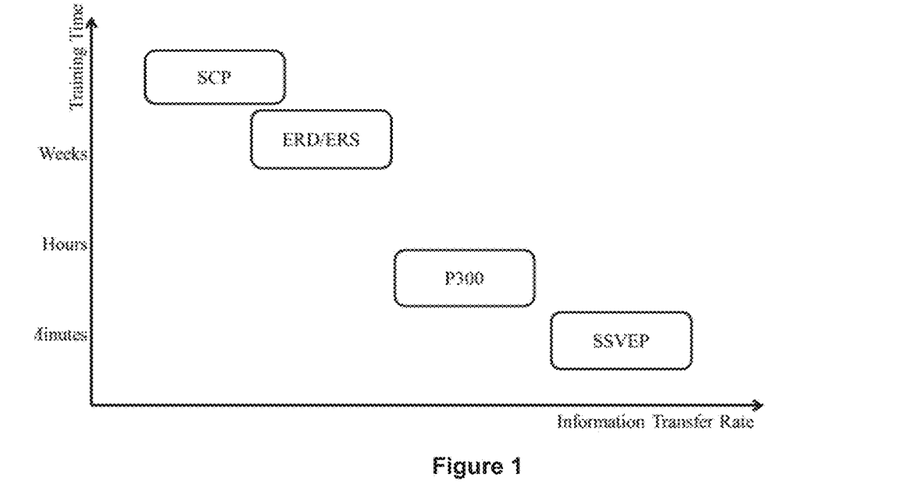
FIG. 1 sets out a general comparison of the different BCI modalities.

FIG. 1 sets out a general comparison of the different BCI modalities. As can be seen, SSVEP technologies provide the fastest transfer rate of the four categories, and the shortest training time.

Figure 2:
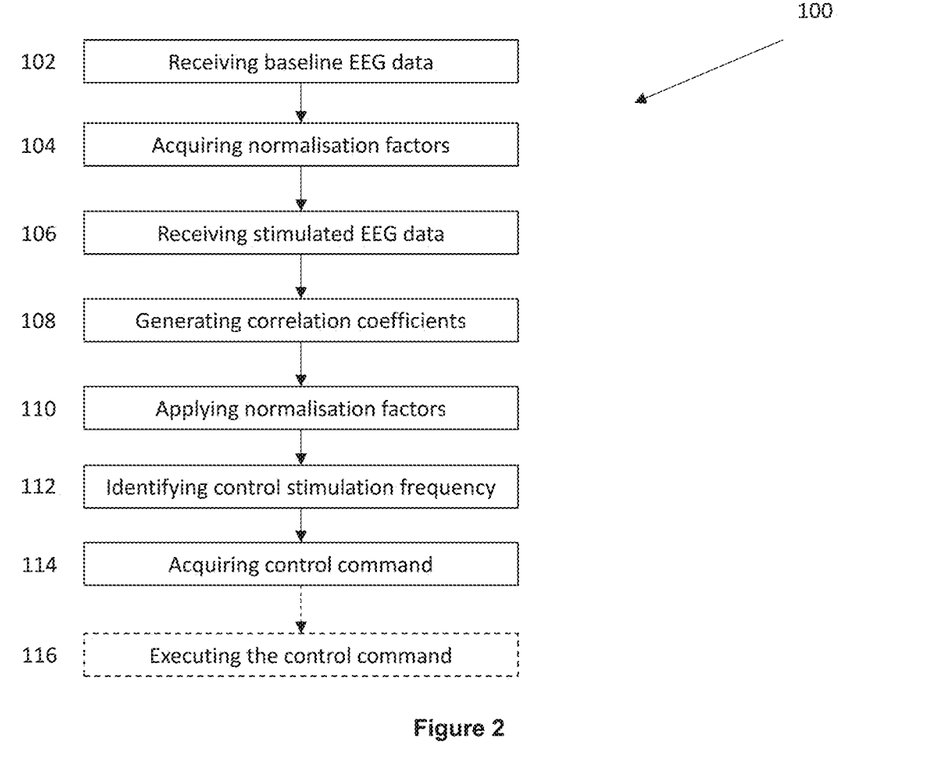
FIG. 2 illustrates a method or computer process—the two terms being used interchangeably herein—for acquiring a control command.

FIG. 2 sets out a computer process 100 for acquiring a control command. The computer process facilitates the normalisation of stimulated EEG data based on a subject-specific baseline. In some embodiments, the computer process provides for the removal of inaccuracies resulting from lag in cortical-response from stimulation time. The process 100 broadly comprises the steps of:
    Step 102: receiving baseline electroencephalogram (EEG) data;
    Step 104: acquire normalizing factors from the baseline EEG data, for spectrum flattening;
    Step 106: receiving stimulated EEG data sensed by one or more EEG sensors;
    Step 108: generating one or more correlation coefficients corresponding to one or more stimulation frequencies;
    Step 110: apply normalization factors to correlation coefficients;
    Step 112: identifying a control stimulation frequency; and
    Step 114: acquiring the control command.

Step 102 involves receiving baseline EEG data. In step 102, as with step 106 in which electroencephalogram (EEG) data is "received", that data may be received by direct input from EEG sensors attached to a subject (e.g. a human) in a known manner. Alternatively, that data may be received by retrieving that data, or by that data being sent, from a database or other system.

The term "baseline" EEG data, and similar, refers to EEG data recorded or sensed while the subject is idle. Thus, the baseline EEG data is not reflective of any particular input or stimulus from the present system or computer process. Conversely, the term "stimulated" EEG data, and similar, refers to EEG data recorded or sensed during a period in which a control command may reasonably be expected. The stimulated EEG data is data that is then analysed to determine if it contains a control command and, in some embodiments, the nature of the control command.

An issue identified by the present inventors is that existing SSVEP BCI implementations attempted to build a general module working across all subjects. Such methods had limitations because reactions to visual stimuli vary from individual to individual. It was found that each individual has a different base spectrum distribution—corresponding to the baseline EEG data received in step 102 which may deteriorate the discriminative feature of CCA-based correlation coefficients. Therefore, subject-specific information may be incorporated to optimize the SSVEP detection.

EEG data sensed by one or more sensors may be retrieved or otherwise received from a database, or may be directly received from the sensors—e.g. in real-time.

Step 104 was developed in view of each individual having EEG signals that, under different situations, scenarios and levels of fatigue, will not have the same characteristics of spectrum distribution. Some effects of this can be observed in FIG. 3a.

Figure 3:
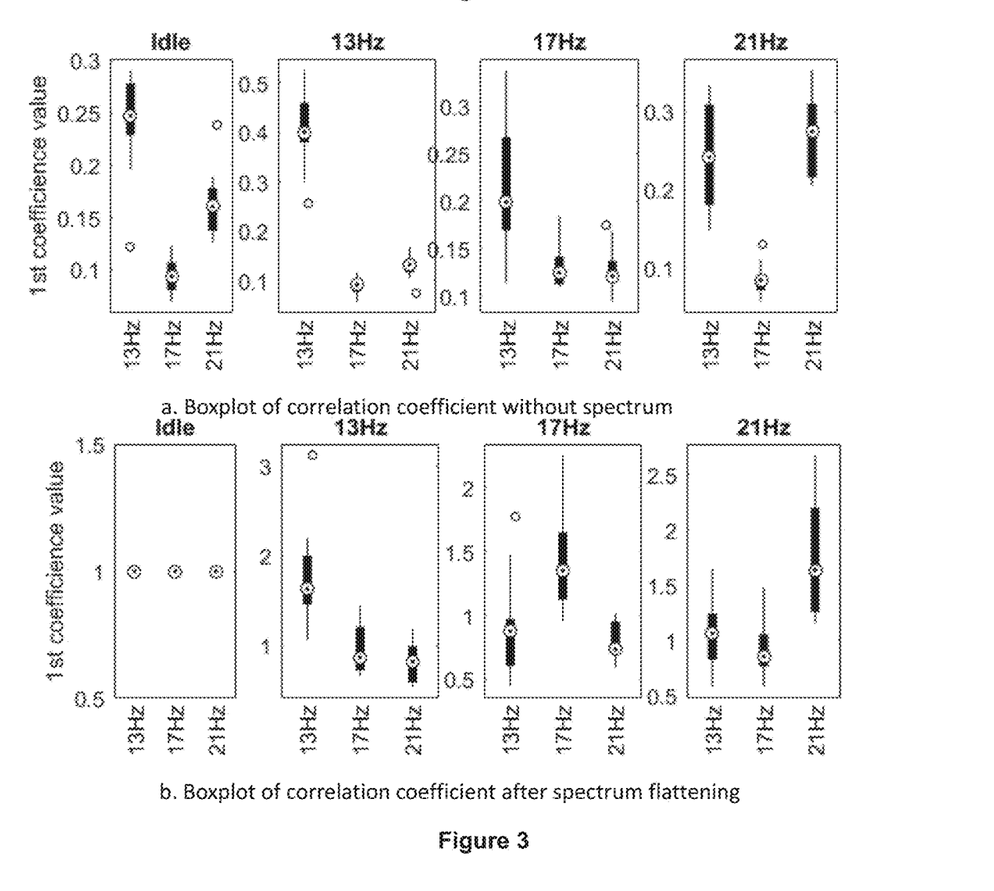
FIG. 3 comprises FIG. 3a, depicting box plots for correlation coefficients determined without using normalisation as taught herein, and FIG. 3b depicting box plots for correlation coefficients determined using normalisation as taught herein.

Considering FIG. 3a, comprising the top group of box plots in FIG. 3 when analysed from left to right, the leftmost subplot shows the correlation coefficient for EEG signals captured from a subject having a relatively higher 13 Hz EEG power ratio when compared with their EEG power ratio at 17 Hz and 21 Hz. The corresponding EEG data was captured while the subject was in an idle state—i.e. without intentional stimulation from the computer system performing the present computer process.

The next subplots show the distributions of EEG power ratios during visual stimulation using 13 Hz, 17 Hz and 21 Hz flickering light respectively. Notably, the discriminative power decreases at 17 Hz, mainly because the subject's base 17 Hz power is rather low. Accordingly, the ability for existing correlation techniques to identify control signals at 17 Hz would be low and unreliable.

The normalization factors determined in accordance with step 104 (discussed below) are intended to flatten the baseline EEG spectrum. An EEG spectrum that is flat will show a substantially consistent baseline spectral power for all relevant stimuli—e.g. the leftmost subplot of FIG. 3a would be the same as the leftmost subplot of FIG. 3b for a flat baseline EEG. As shown in the leftmost subplot of FIG. 3a, however, an individual's actual baseline EEG spectrum (without stimulation) varies from a flat spectrum. With further reference to FIG. 3a, low responsiveness at some stimulation frequencies, such as at 17 Hz, will result in false detection of a command due to the heightened baseline power for other frequencies that have not been stimulated, such as at 13 Hz. The normalizing factors (similarly referred to as normalisation factors) flatten the baseline EEG spectrum as shown in the leftmost subplot of FIG. 3b, so that the idle baseline EEG of an individual has the same, or substantially the same (i.e. sufficient that variation in a particular frequency, resulting from stimulation of the patient, can be attributed to the frequency the power of which, in the stimulated EGG, has increased most), power for all relevant frequencies. Thus the discriminative power of the process is heightened.

Using normalisation or spectrum flattening, as herein taught, the baseline spectrum distribution or baseline EEG data is collected during an initial part of a trial performed on a computer system. Thus, the initial part of the trial will typically correspond to an idle period. The later part of the trial may then consist of the acquisition of control commands based on stimulated EEG data i.e. data generating during periods of the trial where flickering light may be repeatedly or intermittently displayed to the subject and thus the EEG data can reasonably be expected to contain a control command.

Acquisition step 104 involves acquiring normalization factors for adjustment of the correlation coefficients obtained in step 108. Acquisition step 104 may involve analysing the baseline EEG data to produce one or more scaling parameters otherwise referred to as normalization factors. The scaling parameters are then used to flatten correlation coefficients generated for the stimulated EEG data.

To produce the scaling parameters, it is useful to understand the subject's baseline EEG data at particular frequencies. The particular frequencies correspond to frequencies of brainwaves expected to be present in EEG data when a subject endeavours to produce a particular control command.

These particular frequencies are used to produce one or more reference signals. Thus each reference signal has a frequency corresponding to a candidate control command that would be produced if the stimulated EEG data reflected the frequency for that particular control command (i.e. the frequency of highest power, corresponding to the relevant control command) and thus the frequency of the reference signal.

Each scaling parameter is for a particular expected frequency. Thus, each scaling parameter corresponds to a respective reference signal and is determined by comparing the baseline EEG data to the respective reference signal. Once the reference signals have been generated, which may be performed in a pre-existing manner or using a process as discussed with reference to FIG. 7, the idle state EEG signals or baseline EEG signals 400 of FIG. 4, and reference signals 402, can be used in a canonical correlation analysis (CCA) 404 using known techniques.

Figure 4:
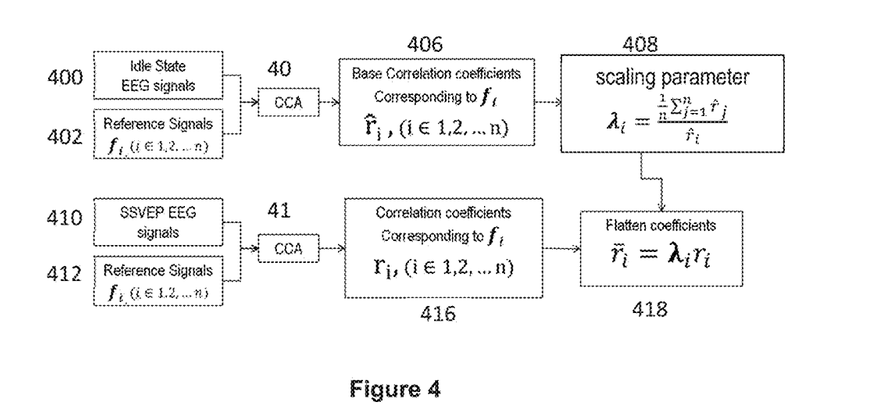
FIG. 4 illustrates a procedure for improving discriminative power—i.e. the ability to distinguish between EEG representing one control command over EEG representing a different control command or no control command.

The result of the CCA 404 produces one or more baseline correlation coefficients 406 each corresponding to a respective one of the one or more reference signals.

The production of relevant baseline correlation coefficients 406 will be understood by the skilled person in view of the present disclosure and with reference to known CCA techniques.

The correlation coefficients specify a correlation between the reference signals and the baseline EEG data, at the frequency of the respective reference signal. The correlation coefficients are then used to determine scaling parameters (i.e. normalisation factors) by which frequencies with high spectral power in a subject's idle state will be deemphasised when compared with frequencies with a lower spectral power in the subject's idle state, to ensure frequencies with a high spectral power do not dominate analysis of subsequently received stimulated EEG data.

The scaling parameters or normalisation factors acquired at step 104 are calculated, at 408, according to the equation:

$$\lambda_i = \frac{\frac{1}{n}\sum_{j=1}^{n} \hat{r}_j}{\hat{r}_i} \qquad \text{(Equation 1)}$$

where $\lambda_i$ is the scaling parameter or normalisation factor for reference signal i, n is the number of reference signals, and $\hat{r}_j$ is the baseline correlation coefficient for reference signal j. If a subject has a particularly high spectrum at the $i^{th}$ frequency, then $\lambda_i$ will be smaller, and vice versa. There is therefore essentially an inverse relationship between a subject's baseline spectral power and $\lambda_i$ for a given frequency. By applying $\lambda_i$, the subjective spectrum distribution can be adjusted or flattened.

Step 106 involves the receipt of stimulated EEG data sensed by one or more EEG sensors. The stimulated EEG data is recorded during periods where the subject may not be idle, such as when a flickering light source is shown to the subject. The stimulated EEG data may therefore contain signals corresponding to control commands.

Per step 108, applying CCA 414 to the stimulated EEG data (i.e. to the data derived from one or more EEG sensors) generates one or more correlation coefficients 416 each corresponding to a respective stimulation frequency and thus to a respective candidate control command. The correlation coefficients specify a correlation between the reference signals and the stimulated EEG data (derived from one or more EEG sensors), at the frequency of the respective reference signal.

To identify the correlation coefficients, the stimulated EEG data (SSVEP EEG signals or stimulated EEG signals) 410 of FIG. 4 are compared to reference signals 412 using known CCA techniques as mentioned above step 414.

The production of the correlation coefficients 416 will be understood by the skilled person in view of the present disclosure and with reference to known CCA techniques.

According to step 110 (set out in broken lines as it may be optional), the correlation is then enhanced to improve discriminative power. This is done by applying the scaling parameters determined according to Equation 1 to the correlation coefficients generated at step 108. This ensures frequencies with a lower spectral power at a subject's idle state are adequately emphasised over frequencies with a higher spectral power at the subject's idle state.

A flattened (i.e. normalised) correlation coefficient is thus generated for each stimulation frequency using the correlation coefficient for the stimulation frequency and the corresponding scaling parameter this is achieved by multiplying the correlation coefficient from 416 by the corresponding scaling parameter from 408, to yield a scaled, normalised or flattened, correlation coefficient 418. This enables a clearer identification of EEG signals resulting from stimulation—i.e. those capable of representing control commands—over EEG signals resulting from a strong spectral power at idle for a particular frequency.

In some embodiments, only a single EEG sensor may be used and thus EEG data is received over a single channel. Where there is stimulated EEG data received from only one sensor, "correlating" that EEG data may simply involve identifying the correlation coefficients of that data against the reference signal(s). The appropriate scaling parameter may still be applied to nevertheless ensure a low spectral power signal is recognisable when stimulated. In embodiments where stimulated EEG data is received from multiple sensors, correlating that data may involve identifying variables that describe or relate the data from each of the multiple sensors and the reference signal(s), in a known manner, and identifying the correlation coefficients from those variables.

Once the flattened correlation coefficients, are produced, a control stimulation frequency is identified—step 112. The control stimulation frequency is taken from one of the control stimulation frequencies each of which corresponds to a control command. The control stimulation frequencies may also correspond to frequencies of the reference signals 402, 412 used in the CCA processes 404, 414 and so to the scaling parameters.

The control stimulation frequency identified at step 112 is the frequency corresponding to the largest flattened correlation coefficient. It is therefore the frequency of the EEG signal considered most likely to correspond to a control command.

A control command is then acquired, step 114, by determining which said candidate control command corresponds to the stimulation frequency with the maximum flattened correlation coefficient. This may be a simple cross-reference to a database or list of control commands and their corresponding stimulation frequencies. The stimulation frequency of a control command is the frequency at which light is flickered in the field of view of the user, and thus the user identifying with the corresponding control will trigger a response in the brain at the frequency of the flicker, and its harmonics.

Once the control command is identified it may be executed, step 116. What is intended by "execution" of the control command will depend on the controllable system through which the control command is executed. For example, where the controllable system is a gaming system, execution of the control command may correspond to movement of a figure on a screen or an action performed by the figure. Where the controllable system is an electric wheelchair or robotic system, execution of the control command may correspond to physical movement of the wheelchair in a particular direction or with a particular speed or acceleration, or may correspond to a predetermined movement of the robotic system.

To facilitate the CCA steps described above, a set of reference signals is required. In some embodiments, a set of reference signals may be produced for a particular frequency based on the sine and cosine of the base frequency and its harmonics such as is shown in Equation 2.

$$Y_1 = \begin{bmatrix} \sin(2\pi * f) \\ \cos(2\pi * f) \\ \sin(2\pi * 2 * f) \\ \cos(2\pi * 2 * f) \\ \ldots \\ \sin(2\pi * m * f) \\ \sin(2\pi * m * f) \end{bmatrix} \qquad \text{Equation 2}$$

where f is the stimulation frequency and m is the number of harmonics, usually m=3. Then CCA calculates the canonical correlation between multi-channel EEGs and $Y_1$ for each stimulation frequency. The resulting stimuli can then be detected.

Despite the foregoing reference signal set going some way to enabling identification of control commands from EEG date, it was found that it takes 600-800 ms for cortical facilitation by visual attention—i.e. response after stimulation. Such time lags vary among different individuals and the approach specified in Equation 2 does not take into consideration the time lag of subject's reaction to visual stimuli.

An alternative approach to generating a set of reference signals, or a reference signal library, is set out in Equation 3.

$$Y_2 = \begin{bmatrix} \sin(2\pi * f) \\ \cos(2\pi * f) \\ \sin(2\pi * f + s_1) \\ \vdots \\ \sin(2\pi * f + s_m) \\ \vdots \\ \cos(2\pi * f + c_1) \\ \vdots \\ \cos(2\pi * f + c_m) \end{bmatrix} \quad \text{Equation 3}$$

where $\{s_i, c_i\}$, $i=1 \ldots m$ are values range in $[-1,1]$, representing the shifting phase of delayed response. This reference signal set includes a plurality of phase-shifted signals for at least one stimulation frequency. The complete reference signal set may comprise at least one phase-shifted signal, or a plurality of phase-shifted signals, for each stimulation frequency.

By providing phase-shifted reference signals, there is a significantly greater likelihood that one of the reference signals will align more closely with the signal of the same frequency in the stimulated EEG data, than with a reference signal of Equation 2 in which each signal is in phase with either the base sine or cosine signal. The reference signal set of Equation 3 thus enables a faster identification of the signal in the EEG data and, accordingly, a faster analysis of the stimulated EEG data. This may enable real-time processing and identification of control commands from stimulated EEG data.

Figure 5:
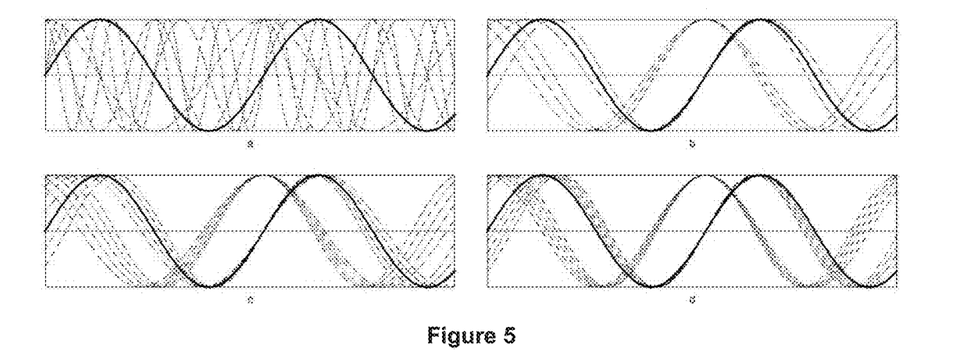
FIGS. 5a-5d show plots for various sets of reference signals.

FIG. 5a shows the reference signals proposed in accordance with Equation 2. The sine signal for the base frequency is prominent, with each harmonic either being in phase with the base sine signal or in phase with its cosine.

FIGS. 5b, 5c and 5d are different proposed reference signal sets, where FIG. 5b includes one reference signal positively phase-shifted and one reference signal negatively phase-shifted from each of the sine and cosine of the base frequency. FIG. 5c includes two reference signals positively phase-shifted and two reference signals negatively phase-shifted from each of the sine and cosine of the base frequency. FIG. 5d shows four reference signals positively phase-shifted from each of the sine and cosine of the base frequency.

The library provides multiple choices for CCA reference signals, enabling optimal detection accuracy for each subject regardless of the cortical-response lag for the subject.

Figure 7:
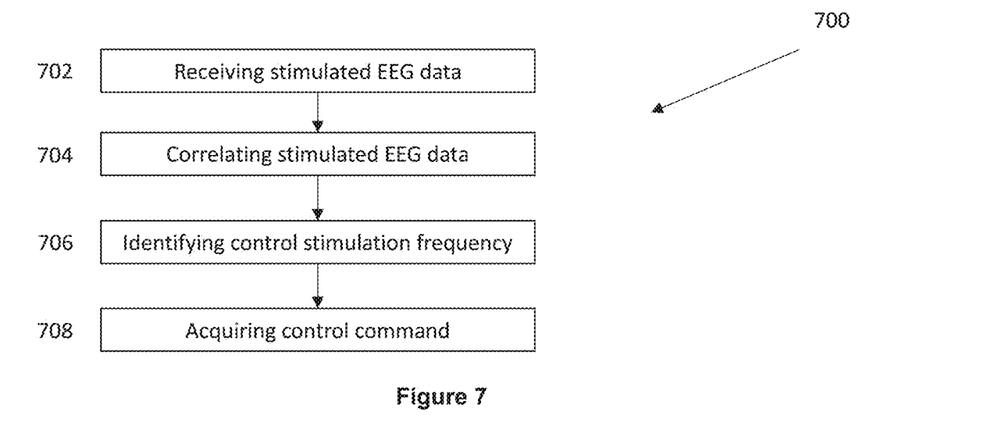
FIG. 7 is a computer process using a plurality of reference signals including phase-shifted reference signals.

FIG. 7 illustrates a computer process 700 in accordance with present teachings, for generating a control command. The process 700 uses an adapted reference signal set such as that constructed in accordance with Equation 3, including at least one phase-shifted reference signal. The process 700 comprises:

Step 702: receiving stimulated EEG data sensed by one or more EEG sensors;

Step 704: correlating the stimulated EEG data across the one or more EEG sensors using, for one or more stimulation frequencies, a plurality of phase-shifted signals of the stimulation frequency, to generate one or more correlation coefficients corresponding to the one or more stimulation frequencies, each of the one or more stimulation frequencies corresponding to a respective candidate control command;

Step 706: identifying, from the one or more stimulation frequencies, a control stimulation frequency based on the one or more correlation coefficients (or flattened correlation coefficient where the correlation coefficients are flattened according to step 110); and Step 708: acquiring the control command by determining which said candidate control command corresponds to the stimulation frequency with the maximum correlation coefficient.

Process 700 may be combined with process 100, or steps in either process may be substituted for steps in the other, and all such variations and modifications are intended to fall within the scope of the present disclosure. For example, steps 102 and 104 may come before step 702. Step 702 may be the same as step 106 and so on.

Figure 6:
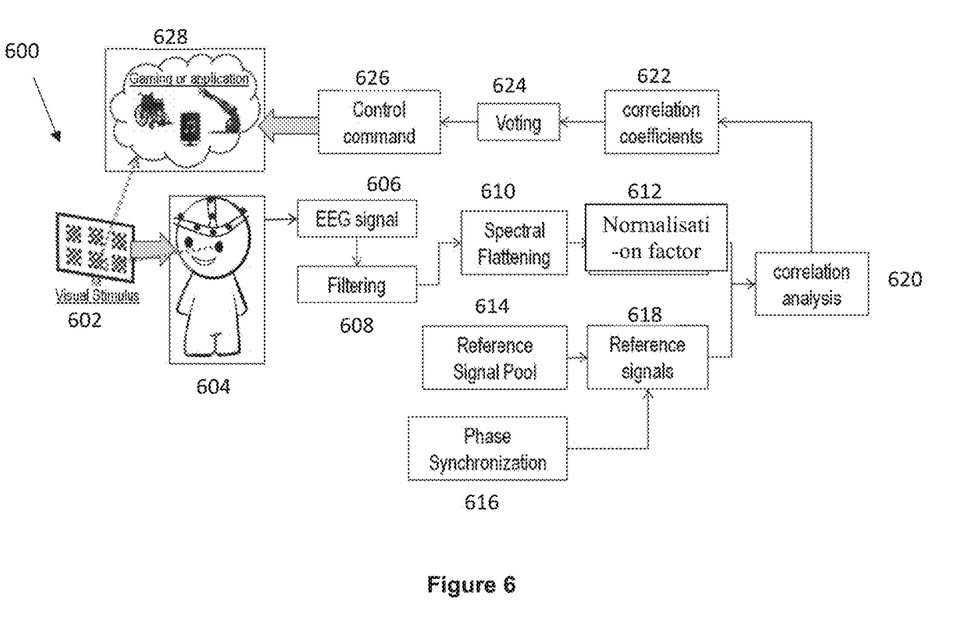
FIG. 6 is a schematic flow diagram of a computer process for acquiring a control command.

FIG. 6 illustrates a schematic diagram 600 corresponding to the processes 100, 700. In FIG. 6 a visual stimulus 602 is shown. The visual stimulus 602 may be, for example, the display of a computer screen or mobile device. The visual stimulus 602 comprises a group of flashing blocks. Each block flashes at a selected frequency—e.g. a reference signal or control command frequency—implying a particular control command for gaming or another application as mentioned above.

A subject 604, to whom the visual stimulus 602 is given, instructs the computer system by looking at the target block. EEG processing then occurs to determine which block the subject is looking at to trigger the control command. The EEG signals are measured—step 606—and are filtered, if desired, in accordance with known techniques—step 608. Scaling parameters are the calculated—step 610—and applied—step 612—to normalise the correlation coefficients. A reference signal pool of base frequencies is generated or extracted/received—step 614—phase synchronisation values $\{s_i, c_i\}$ are determined—step 616—and one or more reference signals are produced—step 618. The reference signals are applied to the stimulated EEG data—correlation analysis step 620—and correlation coefficients extracted—step 622. According to step 622, the correlation coefficients are then normalised or flattened using the normalisation factors acquired at step 612. The flattened correlation coefficients of the stimulated EEG data are then compared (i.e. against each other) to identify the highest flattened correlation coefficient—voting step 624—before acquiring the control command corresponding to that correlation coefficient—step 626. The control command is then—applied step 628—in a manner that depends on the controllable system the command is to control. The controllable system may be the computer system executing the present computer process.

Figure 8:
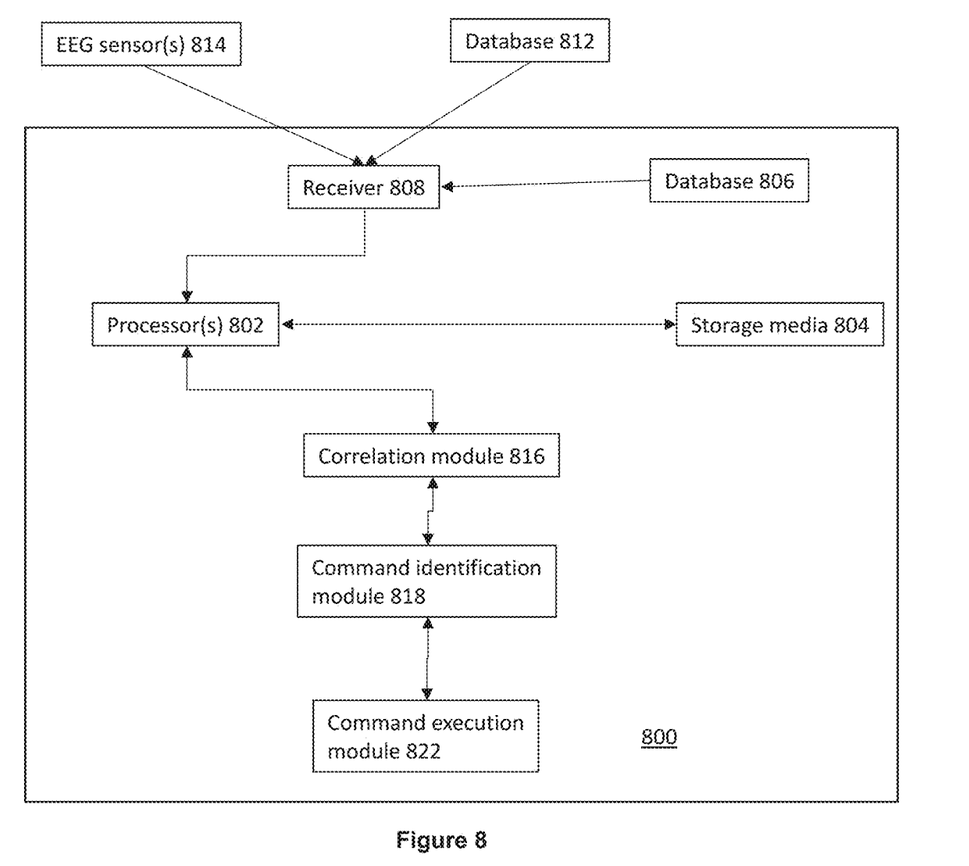
FIG. 8 is a computer system for executing the processes of FIGS. 1 and 7.

FIG. 8 shows a computer system 800 for executing the computer process 100, which may also execute computer process 700. The computer system 800 is used for acquiring a control command, and includes one or more processors 802 in communication with non-transitory data storage media 804. The media 804 stores instructions that, when executed by the one or more processors 802 configure the one or more processors 802 to perform the steps of the process 100, 700.

With reference to the steps specified in processes 100 and 700, the computer system 800 comprises:

an EEG 808 for receiving baseline EEG data and stimulated EEG data sensed by one or more EEG sensors—this data may be received from database 806 within computer system 800, external database 812 or directly from EEG sensors 814 in real-time;

a correlation module 816 for correlating EEG data across the one or more EEG sensors to generate one or more baseline coefficients (in respect of baseline EEG data) or correlation coefficients (in respect of stimulated EEG data) corresponding to one or more stimulation frequencies, each of the one or more stimulation frequencies corresponding to a respective candidate control command; and a normalisation module 810 for acquiring normalisation factors from the baseline EEG data and for normalising the correlation coefficients acquired for the stimulated EEG data using the normalisation factors, to produce flattened correlation coefficients.

The one or more processors are also configured to identify, from the one or more stimulation frequencies, a control stimulation frequency based on the one or more correlation coefficients.

The computer system 800 further comprises a control command identification module 818 for identifying the control command by determining which said candidate control command corresponds to the control stimulation frequency stimulation frequency with the maximum correlation coefficient.

The one or more processors may be configured to generate the scaling parameters or normalisation factors by calculating each the scaling parameter or normalisation factor according Equation 1. The one or more processors may then generate a flattened correlation coefficient for each stimulation frequency using the correlation coefficient for the stimulation frequency and the corresponding scaling parameter. The one or more processors may further identify the control stimulation frequency as being the stimulation frequency with a maximum flattened correlation coefficient.

The computer system 800 may further include a reference signal generation module 820 for generating the one or more reference signals per process 700. The one or more reference signals may therefore include a plurality of phase-shifted signals for at least one of the one or more stimulation frequencies.

The computer system 800 may lastly comprise a command execution module 822 for executing the control command to generate an output in a controllable system.

The controllable system may be the computer system 800 itself, or may be a different system.

Figure 9:
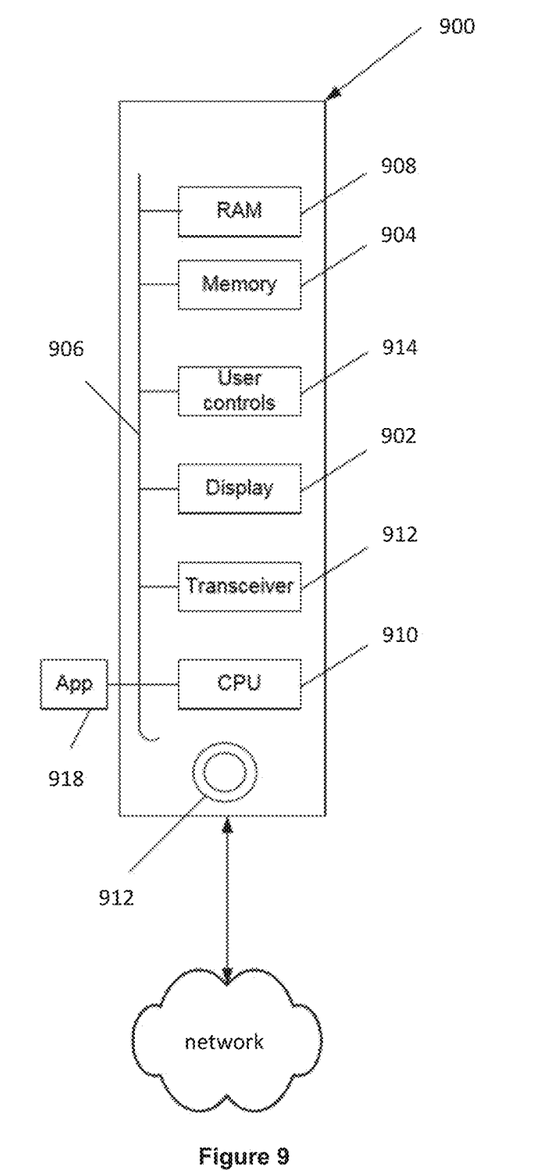
FIG. 9 is a schematic diagram showing components of an exemplary mobile computing device.

FIG. 9 is a block diagram showing an exemplary computer device 900, which may correspond to computer system 800, in which embodiments of the invention may be practiced. The computer device 900 may be a mobile computer device such as a smart phone, a wearable device, a palm-top computer, and multimedia Internet enabled cellular telephones. For ease of description, the computer device is described below, by way of non-limiting example, with reference to a mobile device in the form of an iPhone™ manufactured by Apple™, Inc or one manufactured by LG™, HTC™ and Samsung™, for example.

As shown, the mobile computer device 900 includes the following components in electronic communication via a bus 906:

(a) a display 902;
(b) non-volatile (non-transitory) memory 904;
(c) random access memory ("RAM") 908;
(d) N processing components 910;
(e) a transceiver component 912 that includes N transceivers; and
(f) user controls 914.

The receiver 808, for example, may be performed by the transceiver component 912. The one or more processors 802 of computing device 800 may be performed by the N processing components 910 of mobile computer device 14a, for example.

Although the components depicted in FIG. 9 represent physical components, FIG. 9 is not intended to be a hardware diagram. Thus, many of the components depicted in FIG. 9 may be realized by common constructs or distributed among additional physical components. Moreover, it is certainly contemplated that other existing and yet-to-be developed physical components and architectures may be utilized to implement the functional components described with reference to FIG. 0.

The display 902 generally operates to provide a presentation of content to a user, and may be realized by any of a variety of displays (e.g., CRT, LCD, HDMI, micro-projector and OLED displays).

In general, the non-volatile data storage 904 (also referred to as non-volatile memory) functions to store (e.g., persistently store) data and executable code, and may be none, any or all of media and databases 804, 806 and 812 of computer system 800.

In some embodiments for example, the non-volatile memory 904 includes bootloader code, modem software, operating system code, file system code, and code to facilitate the implementation components, well known to those of ordinary skill in the art, which are not depicted nor described for simplicity.

In many implementations, the non-volatile memory 904 is realized by flash memory (e.g., NAND or ONENAND memory), but it is certainly contemplated that other memory types may be utilized as well. Although it may be possible to execute the code from the non-volatile memory 904, the executable code in the non-volatile memory 904 is typically loaded into RAM 908 and executed by one or more of the N processing components 910.

The N processing components 910 in connection with RAM 908 generally operate to execute the instructions stored in non-volatile memory 904. As one of ordinarily skill in the art will appreciate, the N processing components 910 may include a video processor, modem processor, DSP, graphics processing unit (GPU), and other processing components.

The transceiver component 912 includes N transceiver chains, which may be used for communicating with external devices via wireless networks. Each of the N transceiver chains may represent a transceiver associated with a particular communication scheme. For example, each transceiver may correspond to protocols that are specific to local area networks, cellular networks (e.g., a CDMA network, a GPRS network, a UMTS networks), and other types of communication networks.

The system 900 of FIG. 9 may be connected to any appliance 918, such as EEG sensor(s) 814 or an external database 812 from which baseline and stimulated EEG data may be acquired.

It should be recognized that FIG. 9 is merely exemplary and in one or more exemplary embodiments, the functions described herein may be implemented in hardware, software, firmware, or any combination thereof. If implemented in software, the functions may be stored on or transmitted over as one or more instructions or code encoded on a non-transitory computer-readable medium 904. Non-transitory computer-readable medium 904 includes both computer storage medium and communication medium including any medium that facilitates transfer of a computer program from one place to another. A storage medium may be any available medium that can be accessed by a computer.

Figure 10:
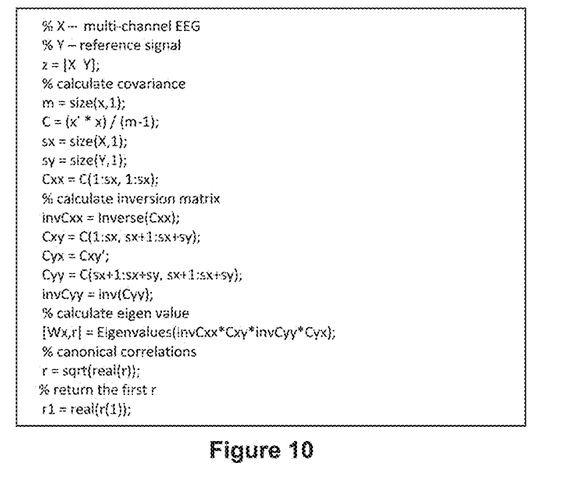
FIG. 10 is pseudo-code for a fast form of CCA.

To facilitate real-time signal processing, a fast version of the original CCA was used to simplify the online processing algorithm. The simplified pseudo code for a fast-CCA is shown in FIG. 10. The calculation of CCA coefficient vectors is simplified into obtaining Eigen values from a covariance matrix.

This fast version of CCA was used in the conduct of analysis on 3 SSVEP data sets as described in table 1. The first 2 data sets are from public servers [14,15]. For the third data set, we design our own data collection experiment, during which, subjects looked at mobile device screen for visual stimulus.

TABLE 1

SSVEP data sets used for analysis

| Data set | Visual Stimuli Flickering Device | Number of subjects | Number of EEG Records | Stimulus frequency |
|---|---|---|---|---|
| Set 1. | LED | 5 | 20 | 13 Hz, 17 Hz, 21 Hz |
| Set 2 | Computer Screen | 4 | 60 | 8 Hz, 14 Hz, 28 Hz |
| Set 3 | Mobile device: Tablet | 5 | 20 | 8, 9, 10, . . . 15 Hz |

Data Set 1: Subjects Viewing Stimulus from Light Emitting Diode (LED)

Figure 11:
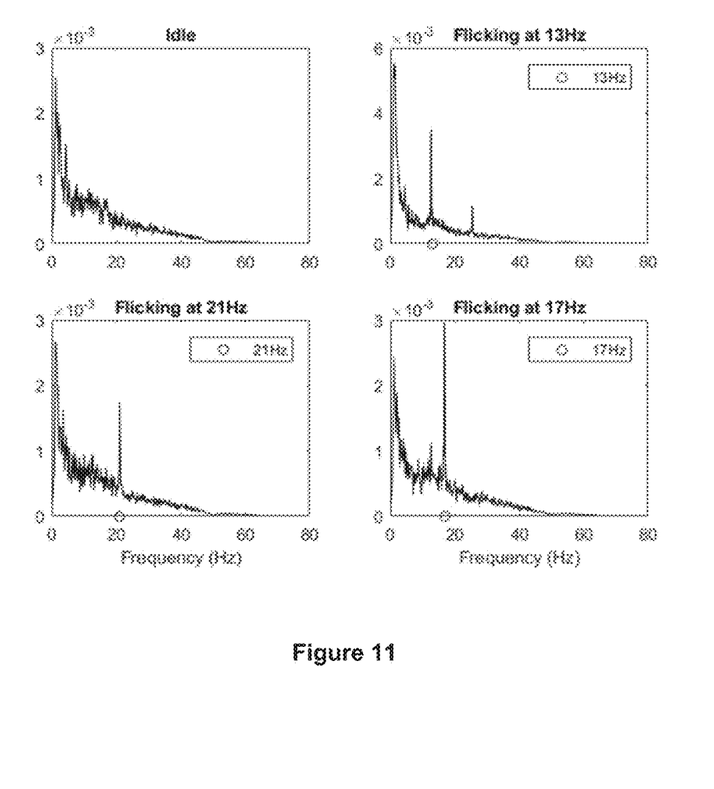
FIG. 11 illustrates spectrum behaviour under idle and SSVEP stimulus according to a first data set.

Data was downloaded from https://datahub.io/dataset/dataset-ssvep-led. This repository includes SSVEP recordings from 5 subjects focusing on 3 groups of LED blinking at different frequencies. During each trial, a subject takes 5 seconds look at stimuli, plus 3 s rest, repeating for 10 trials. Each subject had 4 sessions of record, end up a total of 20 records from 5 subjects. FIG. 11 shows the mean spectrum distributions under idle and SSVEP at different frequencies, acquired by analysing one of the files. This SSVEP EEG shows perfect correlation with all three stimulus.

Experiments were initially conducted on SSVEP detection based on the following configurations:

1. Using 4 channel of data, or 8 channel of data
2. Using 4 different reference signal sets
3. Using flattening module, or no flattening Table 2 shows the results in terms of average accuracy for all 20 records from 5 subjects. The setting for reference signal set 2, which employed the presently taught spectrum flattening or normalisation process, using all 8 channels achieved the most accurate prediction result.

TABLE 2

Mean prediction accuracy on data set 1.

| | flattening = no; channel = 4 | flattening = yes; channel = 4 | flattening = no; channel = 8 | flattening = yes; channel = 8 |
|---|---|---|---|---|
| ref signal 1 | 0.843 | 0.833 | 0.873 | 0.9 |
| ref signal 2 | 0.821 | 0.829 | 0.864 | 0.91 |
| ref signal 3 | 0.773 | 0.839 | 0.805 | 0.908 |
| rei signal 4 | 0.773 | 0.341 | 0.8088 | 0.908 |

Figure 12:
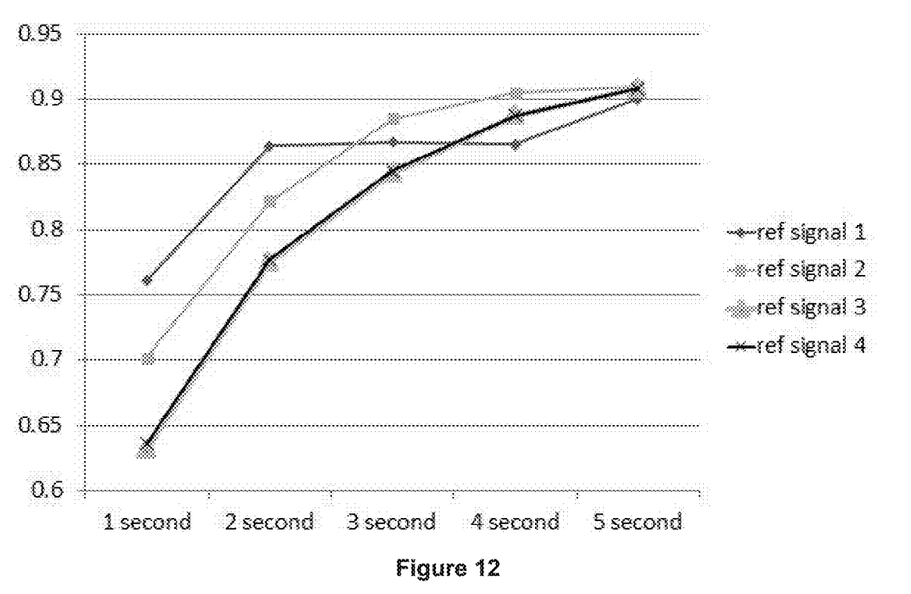
FIG. 12 is the mean prediction accuracy along different time windows for the first data set.

Prediction windows were then analysed to determine the improvement or declination in accuracy over time. 1 to 5 second epochs of EEG data were acquired for the prediction, to understand which reference signals can yield a faster prediction. At 3 seconds, reference signal set 2 reaches the accuracy of 0.885, while the default reference signal, performs less well. The result is shown in FIG. 12.

Data Set 2: Subjects Viewing Stimulus from Computer Screen

Data from http://www.bakardjian.com/work/ssvep_data-_Bakardiian.html was acquired for this test. The EEG data was collected by research intending to investigate the time dynamics of the stimulation frequency on the SSVEP response. 4 subjects each conducted 3 sets of trial for 3 stimuli frequencies, e.g., 8 Hz, MHz and 28 Hz. In total, 60 files were available for analysis. Since 14 Hz and 28 Hz are harmonic frequencies, this data is treated as a bi-class problem, and MHz and 8 Hz are used to compose reference signals.

Experiment was first conducted on SSVEP detection based on the following settings:

1. Using 4, 12 or all 128 channels of data
2. Using 4 different reference signal sets
3. Using flattening module, or no flattening Table 3 shows the result in terms of average accuracy for all 60 records from 4 subjects. The setting of reference signal set 4, again employing the presently taught spectrum flattening process, and using all 128 channels achieves the best prediction result.

TABLE 3

Mean prediction accuracy on data set 2.

| class = 2 14, 28 vs 8 Hz | flattening = no; channel = 4 | flattening = no; channel = 12 | flattening = no; channel = 128 | flattening = yes; channel = 4 | flattening = yes; channel = 12 | flattening = yes; channel = 128 |
|---|---|---|---|---|---|---|
| ref signal 1 | 0.525 | 0.575 | 0.475 | 0.6 | 0.625 | 0.5 |
| ref signal 2 | 0.625 | 0.75 | 0.55 | 0.725 | 0.875 | 0.925 |
| ref signal 3 | 0.775 | 0.9 | 0.925 | 0.825 | 0.9 | 0.975 |
| ref signal 4 | 0.825 | 0.925 | 0.975 | 0.825 | 0.9 | 1 |

Figure 13:
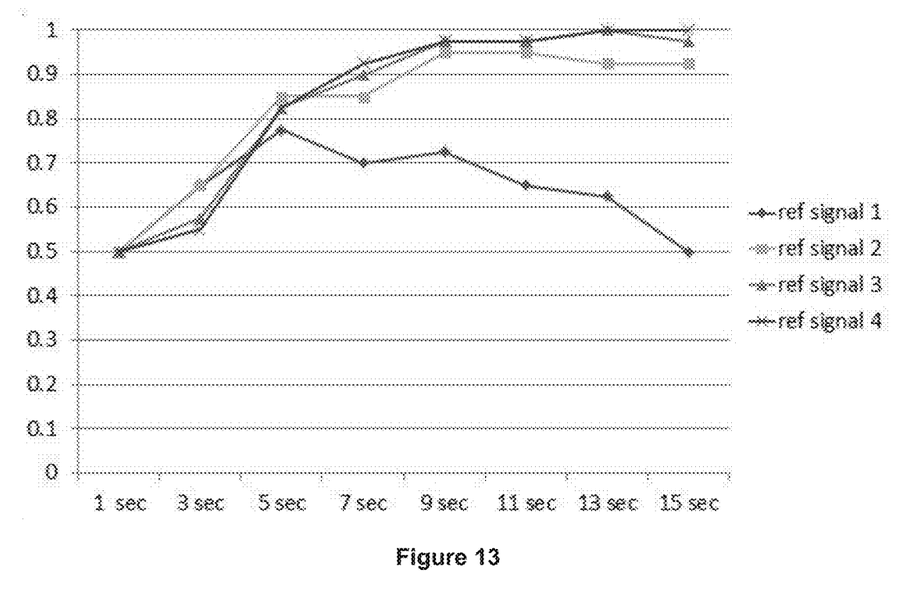
FIG. 13 illustrates mean prediction accuracy along different time windows for a second data set.

Prediction window analysis was then conducted. For the prediction, 1 to 15 second epochs were collected over 8 channels of EEG data to understand which reference signals can yield a faster prediction. As shown in FIG. 13, after 5 seconds, reference signal set 4 persistently outperforms all other signals sets.

Data Set 3: Subjects Viewing Stimulus from Mobile Device

Lastly, an experiment was designed to collect mobile device SSVEP data to determine a prediction accuracy on a mobile platform. An Android tablet was used to provide a flickering stimulus. 4 subjects each conducted 2 sessions of static and 2 sessions of dynamic flickering stimulus of 8, 9, 10, 11, 12, 13, 14 and 15 Hz. In each trial, the subject looks at the flickering source for 10 seconds, followed by a 1 second rest, repeating for 8 trials. In total, 16 files were available for analysis.

Figure 14:
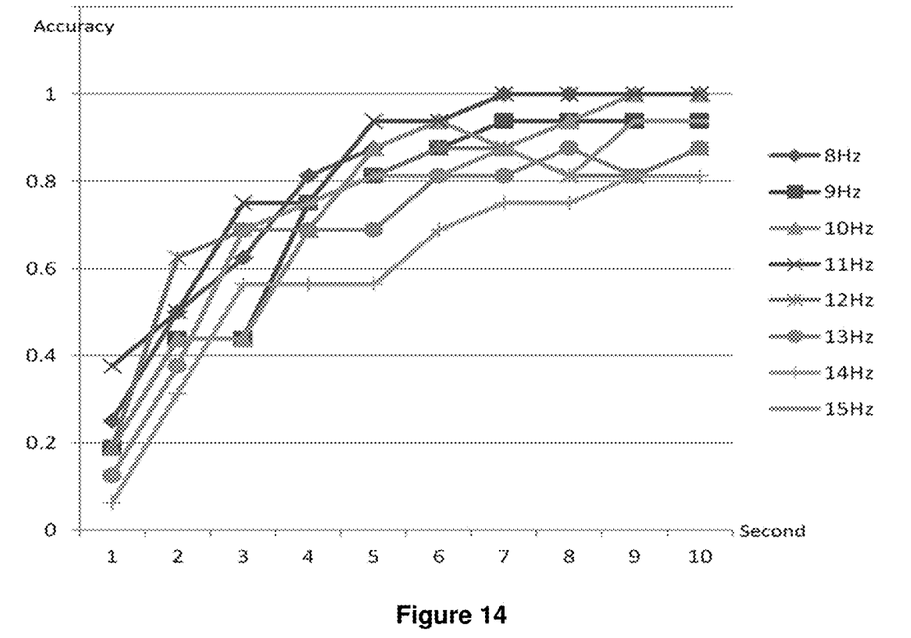
FIG. 14 illustrates prediction accuracy of different stimuli across all subjects along various time windows.
Figure 15:
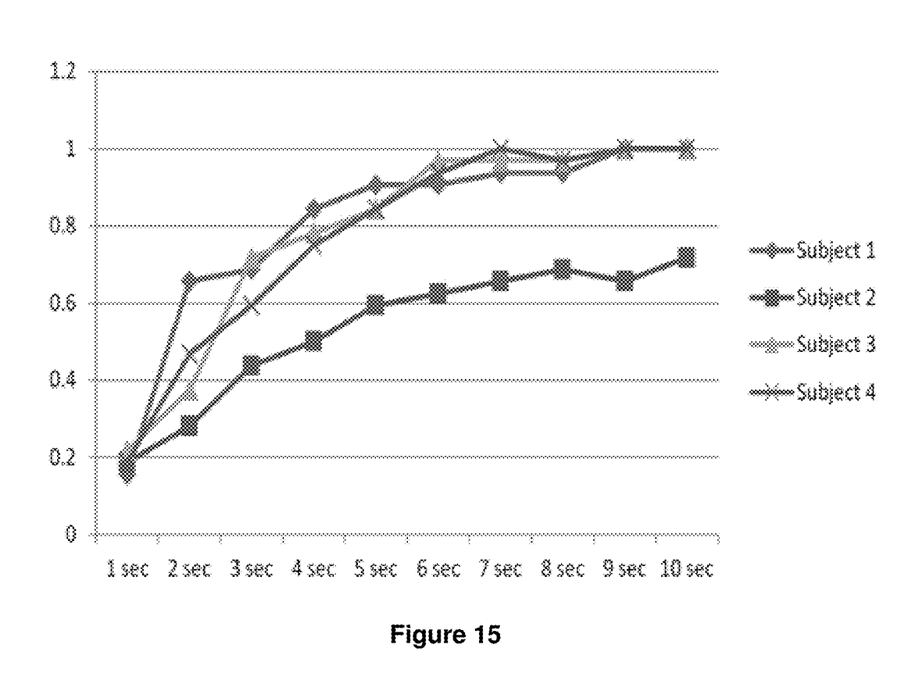
FIG. 15 illustrates the accuracy for four subjects for all sub-stimuli along the various time windows.

This trial scheme achieved a mean prediction accuracy of 93% for a 10 second prediction window. At 5 seconds, the mean prediction accuracy was 79.7%. FIGS. 14 and 15 show, respectively, the accuracy for different stimuli across all subjects, and the accuracy for each subjects across all stimuli, along the time windows.

Embodiments of the present invention thus provide a subject specific, and device specific, highly accurate self-paced BCI for gaming and control i.e. the acquisition of control commands from EEG data. Embodiments of the present invention:

- incorporate cross-subject heterogeneity of spectrum distribution into the analyses to improve the prediction accuracy;
- perform spectrum flattening to improve discriminative power for SSVEP detection;
- permit subject-specific cortical response time lag compensation by composing a library of phase shifting reference signals and, more specifically, by composing CCA reference signals taking into account time lag of subject's reaction to visual stimuli;
- permit optimisation for any flickering source device (including LED, computer screen and mobile devices) using a flexible reference signal set generating method;
- permit optimization of detection accuracy for different subjects by selecting one of multiple of the composed CCA reference signal; and/or
- provide a fast process of CCA for real-time signal processing and, more specifically, a fast CCA which uses Eigen values from a covariance matrix instead of CCA coefficient vectors.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that the prior art forms part of the common general knowledge.

The invention claimed is:

1. A computer system for acquiring a control command, the system including one or more processors in communication with non-transitory data storage media having instructions stored thereon that, when executed by the one or more processors configure the one or more processors to perform the steps of:
    receiving, at an electroencephalogram (EEG) receiver, baseline EEG data;
    acquiring, using a normalisation module, one or more normalisation factors from the baseline EEG data;
    receiving, at the EEG receiver, stimulated EEG data sensed by one or more EEG sensors;
    correlating the stimulated EEG data across the one or more EEG sensors, using a correlation module, to generate one or more correlation coefficients corresponding to one or more stimulation frequencies, each of the one or more stimulation frequencies corresponding to a respective candidate control command;
    applying the one or more normalisation factors to the one or more correlation coefficients to produce one or more flattened correlation coefficients;
    identifying, from the one or more stimulation frequencies and using the one or more processors, a control stimulation frequency based on the one or more flattened correlation coefficients; and
    acquiring, using a control command identification module, the control command by determining which said candidate control command corresponds to the control stimulation frequency.

2. The computer system according to claim 1, wherein each normalisation factor of the one or more normalisation factors corresponds to a respective reference signal, wherein the normalisation module acquires the one or more normalisation factors by comparing the baseline EEG data to the respective reference signal.

3. The computer system according to claim 2, wherein each reference signal corresponds to a said candidate control command.

4. The computer system according to claim 2, wherein the normalisation module acquires the one or more normalisation factors by determining one or more baseline correlation coefficients each corresponding to a respective one of the one or more reference signals.

5. The computer system according to claim 4, wherein the normalisation module acquires each normalisation factor by calculating the respective normalisation factor according to the equation:

$$\lambda_i = \frac{\frac{1}{n}\sum_{j=1}^{n}\hat{r}_j}{\hat{r}_i}$$

where $\lambda_i$ is the normalisation factor for reference signal i, n is the number of stimuli frequencies, and $\hat{r}_i$ is the baseline correlation coefficient for reference signal i.

6. The computer system according to claim 2, wherein each said stimulation frequency corresponds to a said respective reference signal and thereby to the normalisation factor and flattened correlation coefficient corresponding to the respective reference signal.

7. The computer system according to claim 6, wherein the one or more processors identify the control stimulation frequency as being the stimulation frequency with a maximum flattened correlation coefficient.

8. The computer system according to claim 2, further comprising a reference signal generation module for generating the one or more reference signals to include a plurality of phase-shifted signals for at least one of the one or more stimulation frequencies.

9. The computer system according to claim 8, wherein the one or more reference signals include a plurality of phase-shifted signals for each stimulation frequency of the one or more stimulation frequencies.

10. The computer system according to claim 1, further comprising a command execution module for executing the control command to generate an output in a controllable system.

11. A computer process for acquiring a control command, comprising:
    receiving baseline electroencephalogram (EEG) data;
    acquiring one or more normalisation factors from the baseline EEG data;

receiving stimulated EEG data sensed by one or more EEG sensors;

correlating the normalised EEG data across the one or more EEG sensors to generate one or more correlation coefficients corresponding to one or more stimulation frequencies, each of the one or more stimulation frequencies corresponding to a respective candidate control command;

applying the one or more normalisation factors to the one or more correlation coefficients to produce one or more flattened correlation coefficients;

identifying, from the one or more stimulation frequencies, a control stimulation frequency based on the one or more flattened correlation coefficients; and acquiring the control command by determining which said candidate control command corresponds to the control stimulation frequency.

12. The computer process according to claim 11, wherein each normalisation factor of the one or more normalisation factors corresponds to a respective reference signal, and acquiring the one or more normalisation factors comprises comparing the baseline EEG data to the respective reference signal.

13. The computer process according to claim 12, wherein each reference signal corresponds to a said candidate control command.

14. The computer process according to claim 12, wherein acquiring the one or more normalisation factors further comprises determining one or more baseline correlation coefficients each corresponding to a respective one of the one or more reference signals.

15. The computer process according to claim 14, wherein acquiring each normalisation factor comprises calculating the said normalisation factor according to the equation:

$$\lambda_i = \frac{\frac{1}{n}\sum_{j=1}^{n} \hat{r}_j}{\hat{r}_i}$$

where $\lambda_i$ is the normalisation factor for reference signal i, n is the number of stimuli frequencies, and $\hat{r}_i$ is the baseline correlation coefficient for reference signal i.

16. The computer process according to claim 12, wherein each said stimulation frequency corresponds to a said respective reference signal and thereby to the normalisation factor and flattened correlation coefficient corresponding to the respective reference signal.

17. The computer process according to claim 16, wherein the control stimulation frequency is the stimulation frequency with a maximum flattened correlation coefficient.

18. The computer process according to claim 12, wherein the one or more reference signals include a plurality of phase-shifted signals for at least one, and preferably each, of the one or more stimulation frequencies.

19. The computer process according to claim 11, further comprising executing the control command to generate an output in a controllable system.

20. A computer process for generating a control command, comprising:

receiving stimulated EEG data sensed by one or more EEG sensors;

correlating the stimulated EEG data across the one or more EEG sensors using, for one or more stimulation frequencies, a plurality of phase-shifted signals of the stimulation frequency, to generate one or more correlation coefficients corresponding to the one or more stimulation frequencies, each of the one or more stimulation frequencies corresponding to a respective candidate control command;

identifying, from the one or more stimulation frequencies, a control stimulation frequency based on the one or more correlation coefficients; and acquiring the control command by determining which said candidate control command corresponds to the stimulation frequency with the maximum correlation coefficient.

* * * * *